US010391304B2

(12) United States Patent
Flowers et al.

(10) Patent No.: US 10,391,304 B2
(45) Date of Patent: Aug. 27, 2019

(54) NEUROSTIMULATION LEAD WITH STIFFENED PROXIMAL ARRAY

(71) Applicant: Boston Scientific Neuromodulation Corporation, Valencia, CA (US)

(72) Inventors: Matthew Braden Flowers, Irvine, CA (US); John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 474 days.

(21) Appl. No.: 15/206,073

(22) Filed: Jul. 8, 2016

(65) Prior Publication Data
US 2016/0317804 A1 Nov. 3, 2016

Related U.S. Application Data

(63) Continuation of application No. 11/963,650, filed on Dec. 21, 2007, now Pat. No. 9,399,127.

(51) Int. Cl.
*A61N 1/05* (2006.01)
*A61N 1/375* (2006.01)
*A61M 25/00* (2006.01)

(52) U.S. Cl.
CPC ......... *A61N 1/0551* (2013.01); *A61N 1/3752* (2013.01); *A61M 2025/0059* (2013.01)

(58) Field of Classification Search
CPC .............................. A61N 1/0551; A61N 1/056
See application file for complete search history.

(56) References Cited

U.S. PATENT DOCUMENTS 4,046,151 A 9/1977 Rose
4,379,462 A * 4/1983 Borkan ................ A61N 1/0551
607/117

(Continued)

FOREIGN PATENT DOCUMENTS

WO WO 90/02581 3/1990
WO WO 91104069 4/1991
(Continued)

OTHER PUBLICATIONS

Official Communication for U.S. Appl. No. 11/963,650, dated Aug. 1, 2012.
(Continued)

*Primary Examiner* — Michael J D Abreu
(74) *Attorney, Agent, or Firm* — Lowe Graham Jones PLLC; Bruce E. Black

(57) ABSTRACT

An implantable electrical lead is provided. The electrical lead comprises an electrically insulative, flexible, elongated lead body having a proximal end and a distal end, an electrical contact carried by the distal end of the lead body, an electrical terminal carried by the proximal end of the lead body, an electrical conductor axially extending within the lead body between the electrical contact and the electrical terminal, and a stiffening tube extending within the proximal end of the lead body from a point proximal to the terminal to a point distal to the terminal and proximal to the electrode. An implantable lead assembly kit comprises the implantable electrical lead, and a connector configured for firmly receiving the proximal end of the lead body. A method of implanting the electrical lead comprises introducing the electrical lead into a patient.

20 Claims, 8 Drawing Sheets

(56) References Cited

U.S. PATENT DOCUMENTS

| | | |
|---|---|---|
| 4,934,366 A | 6/1990 | Truex et al. |
| 5,827,278 A | 10/1998 | Webster, Jr. |
| 6,356,791 B1 | 3/2002 | Westlund et al. |
| 6,549,812 B1 * | 4/2003 | Smits .................... A61N 1/056 607/122 |
| 6,556,873 B1 | 4/2003 | Smits |
| 6,741,893 B2 | 5/2004 | Smits |
| 6,968,237 B2 | 11/2005 | Doan et al. |
| 7,089,065 B2 | 8/2006 | Westlund et al. |
| 7,244,150 B1 | 7/2007 | Brase et al. |
| 7,328,069 B2 | 2/2008 | Gerber |
| 2002/0077686 A1 | 6/2002 | Westlund et al. |
| 2003/0220677 A1 | 11/2003 | Doan et al. |
| 2004/0162601 A1 | 8/2004 | Smits |
| 2005/0027343 A1 | 2/2005 | Westlund et al. |
| 2005/0080471 A1 | 4/2005 | Chitre et al. |
| 2006/0089692 A1 | 4/2006 | Cross, Jr. et al. |
| 2006/0089695 A1 | 4/2006 | Bolea et al. |
| 2006/0089697 A1 * | 4/2006 | Cross, Jr. ............... A61N 1/056 607/122 |
| 2007/0150036 A1 | 6/2007 | Anderson |
| 2007/0161294 A1 | 7/2007 | Brase et al. |
| 2007/0168004 A1 | 7/2007 | Walter |
| 2007/0168007 A1 | 7/2007 | Kuzma |

FOREIGN PATENT DOCUMENTS

| | | |
|---|---|---|
| WO | WO 99/64100 | 12/1999 |
| WO | WO 2006/047168 | 5/2006 |
| WO | WO 2006/047178 | 5/2006 |
| WO | WO 2006/047179 | 5/2006 |
| WO | WO 2007/027879 | 3/2007 |

OTHER PUBLICATIONS

Official Communication for U.S. Appl. No. 11/963,650, dated Feb. 1, 2012.

Official Communication for U.S. Appl. No. 11/963,650, dated Aug. 16, 2011.

Official Communication for U.S. Appl. No. 11/963,650, dated Apr. 27, 2011.

Official Communication for U.S. Appl. No. 11/963,650, dated Dec. 23, 2010.

* cited by examiner

NEUROSTIMULATION LEAD WITH STIFFENED PROXIMAL ARRAY

CROSS REFERENCE TO RELATED APPLICATIONS

This application is a continuation of U.S. patent application Ser. No. 11/963,650 filed Dec. 21, 2007, now U.S. Pat. No. 9,399,127, which is incorporated herein by reference in its entirety.

FIELD OF THE INVENTION

The present invention relates to tissue stimulation systems, and more particularly, to neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more stimulation leads implanted at the desired stimulation site. In the context of an SCS procedure, one or more stimulation leads are introduced through the patient's back into the epidural space under fluoroscopy, such that the electrodes carried by the leads are arranged in a desired pattern and spacing to create an electrode array.

The specific procedure used to implant the stimulation leads in an SCS procedure will ultimately depend on the type of stimulation leads used. Currently, there are two types of commercially available stimulation leads: a percutaneous lead and a surgical lead.

A percutaneous lead comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline. In many cases, a stylet, such as a metallic wire, is inserted into a lumen running through the center of each of the percutaneous leads to aid in insertion of the lead through the needle and into the epidural space. The stylet gives the lead rigidity during positioning, and once the lead is positioned, the stylet can be removed after which the lead becomes flaccid.

A surgical lead has a paddle on which multiple electrodes are arranged in independent columns, and is introduced into contact with the affected spinal tissue using a surgical procedure, and specifically, a laminectomy, which involves removal of the laminar vertebral tissue to allow both access to the dura layer and positioning of the lead.

Each of the above-mentioned implantable neurostimulation systems also comprises an implantable neurostimulator, such as an implantable pulse generator (IPG), implanted remotely from the stimulation site, but coupled to the stimulation leads. Thus, electrical pulses can be delivered from the neurostimulator to the stimulation leads to stimulate the tissue and provide the desired efficacious therapy to the patient. In the context of an SCS procedure, the electrical pulses are delivered to the dorsal column and dorsal root fibers within the spinal cord. The stimulation creates the sensation known as paresthesia, which can be characterized as an alternative sensation that replaces the pain signals sensed by the patient.

Each stimulation lead may be directly coupled to the neurostimulator or indirectly coupled to the neurostimulator via an extension leads.

If the stimulation leads are to be directly connected to the neurostimulator, the proximal ends of the stimulation leads can be inserted into a connector of the neurostimulator, such that the terminals located at the proximal ends of the stimulation leads are coupled to corresponding electrical contacts within the connector. Individual wires are routed though lumens in each stimulation lead to connect the proximally-located terminals with the distally-located electrodes.

If the stimulation leads are to be indirectly connected to the neurostimulator via the extension leads, the proximal ends of the stimulation leads can be inserted into connectors located at the distal ends of the respective extension leads, such that the terminals of the stimulation leads are coupled to corresponding electrical contacts within the connectors of the extension leads. The proximal ends of the extension leads can then be inserted into the connector of the neurostimulator, such that terminals located at the proximal ends of the extension leads are coupled to the corresponding electrical contacts within the connector of the neurostimulator. Individual wires are routed though lumens in each extension lead to respectively couple the proximally-located terminals to the distally-located electrical contacts.

To facilitate introduction of the proximal end of a stimulation lead or extension lead into a corresponding connector, it is desirable that the proximal end be as stiff as reasonably possible to provide the necessary columnar strength for the proximal end to overcome the frictional forces exerted on the lead when inserted into the connector. Simply put, adding stiffness to the proximal end of an electrical lead allows the physician to easily mate the lead with the connector by grasping the proximal end of the lead and inserting it into the connector without buckling the lead within the physician's hand. At the same time, it is important that the remaining portion of the lead be as flexible as reasonably possible, so as to minimize the possibility of tissue trauma/irritation to the epidural and surrounding tissues.

Currently, in the context of SCS procedures, the proximal end of each electrical lead is stiffened by backfilling lumens through which the conductors between the electrodes and terminals extends with an epoxy, such as Hysol® epoxy. While Hysol® epoxy provides some stiffness increase to the proximal end of the electrical lead, it is limited by the physical properties of the resin and requires time consuming processing steps (precise mixing and heat curing) in manufacturing.

There, thus, remains a need for an alternative method for stiffening the proximal end of an electrical lead, such as a stimulation lead or an extension lead.

SUMMARY OF THE INVENTION

In accordance with one aspect of the present inventions, an implantable electrical lead is provided. The electrical lead comprises an electrically insulative, flexible, elongated lead body having a proximal end and a distal end. The electrical lead further comprises an electrical contact carried by the distal end of the lead body. In one embodiment, the electrical contact is an electrode. In another embodiment, the electrical lead further comprises a connector carried by the distal end of the lead body, in which case, the electrical contact is contained within the connector. The electrical lead further comprises an electrical terminal carried by the proximal end of the lead body, and an electrical conductor axially extending within the lead body between the electrical contact and the electrical terminal.

The electrical lead further comprises a stiffening tube extending within the proximal end of the lead body from a point proximal to the terminal to a point distal to the terminal and proximal to the electrode. In one embodiment, the electrical lead comprises a plurality of electrical contacts carried by the distal end of the lead body, a plurality of electrical terminals carried by the proximal end of the lead body, and a plurality of electrical conductors axially extending within the lead body between the respective electrical contacts and the respective electrical terminals, in which case, the stiffening tube may extend from a point proximal to the plurality of terminals to a point distal to the plurality of terminals and proximal to the plurality of electrodes.

In one embodiment, the stiffening tube and lead body are concentrically disposed relative to each other. In another embodiment, electrical lead further comprises a central lumen extending within the proximal end of the lead body, in which case, the stiffening tube may surround the central lumen. The stiffening tube may be composed of any relatively stiff material, such as a metallic material. The electrical lead may comprise a retention sleeve mounted to the proximal end of he lead body distal to the electrical contact, in which case, the stiffening tube may terminate in the lead body at or distal to the retention sleeve. In an optional embodiment, the electrical lead further comprises a coil extending within the proximal end of the lead body distal to the stiffening tube. The coil may be connected to the stiffening tube.

While the present inventions should not be so limited in their broadest aspects, the stiffening tube provides an effective means for stiffening the proximal end of a stimulation lead without having to use a pre-mixed injected resin filler material. In addition, the coil may provide a strain relief for the stiffening tube, as well as providing some stiffness to the proximal end of the stimulation lead for a physician to grasp.

In accordance with another aspect of the present inventions, an implantable lead assembly kit is provided. The kit comprises the previously described implantable electrical lead and a connector configured for firmly receiving the proximal end of the lead body. In one embodiment, the stiffening tube is configured for being completely disposed within the connector when the proximal end of the lead body is fully received within the connector. In another embodiment, the electrical lead further comprises a coil extending within the proximal end of the lead body distal to the stiffening tube, in which case, the coil may be configured for extending distally from the connector when the proximal end of the lead body is fully received within the connector. In another embodiment, the electrical contact is an electrode, in which case, the kit may further comprise an extension lead that carries the connector. In still another embodiment, the kit further comprises a neurostimulator that carries the connector.

In accordance with a third aspect of the present inventions, a method of using the previously described electrical lead is provided. The method comprises introducing the electrical lead into a patient. One method may further comprise inserting the proximal end of the lead body into a connector having an electrical contact that contacts the electrical terminal. The connector may be carried by a neurostimulator, in which case, the method may further comprise providing therapy to the patient by conveying electrical energy from the neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
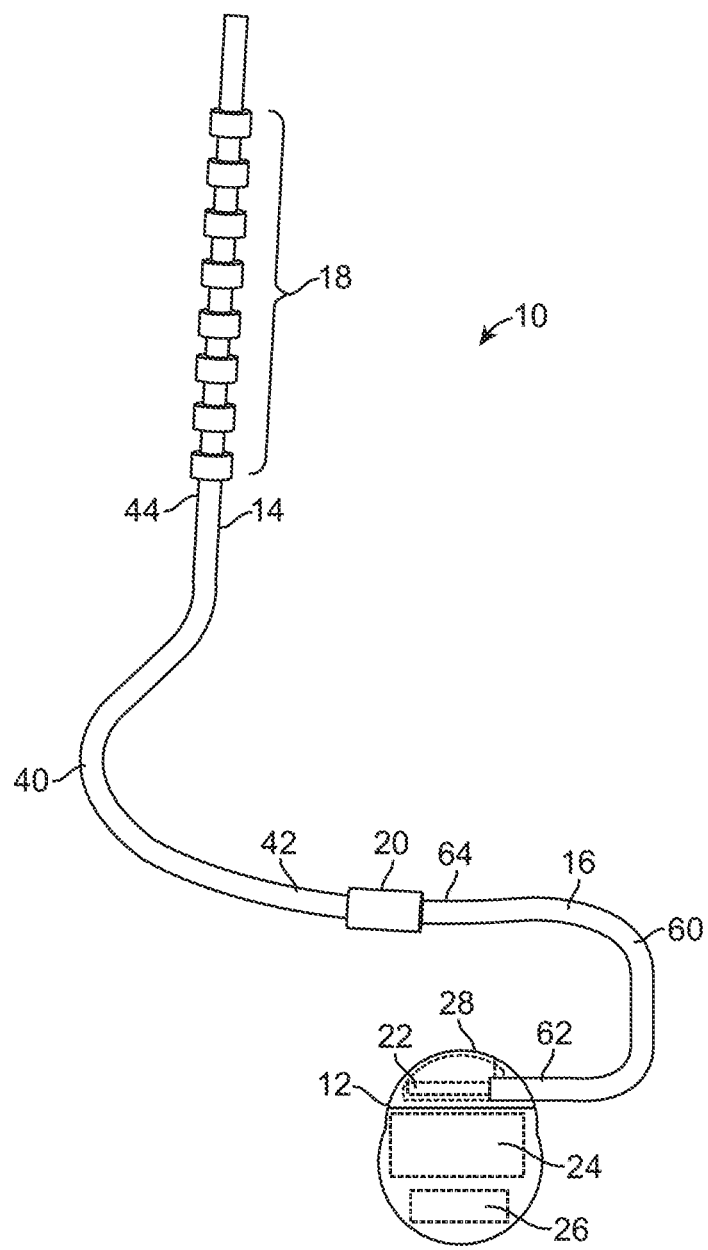
FIG. 1 is plan view of one embodiment of a tissue stimulation system constructed in accordance with the present inventions.
Figure 2:
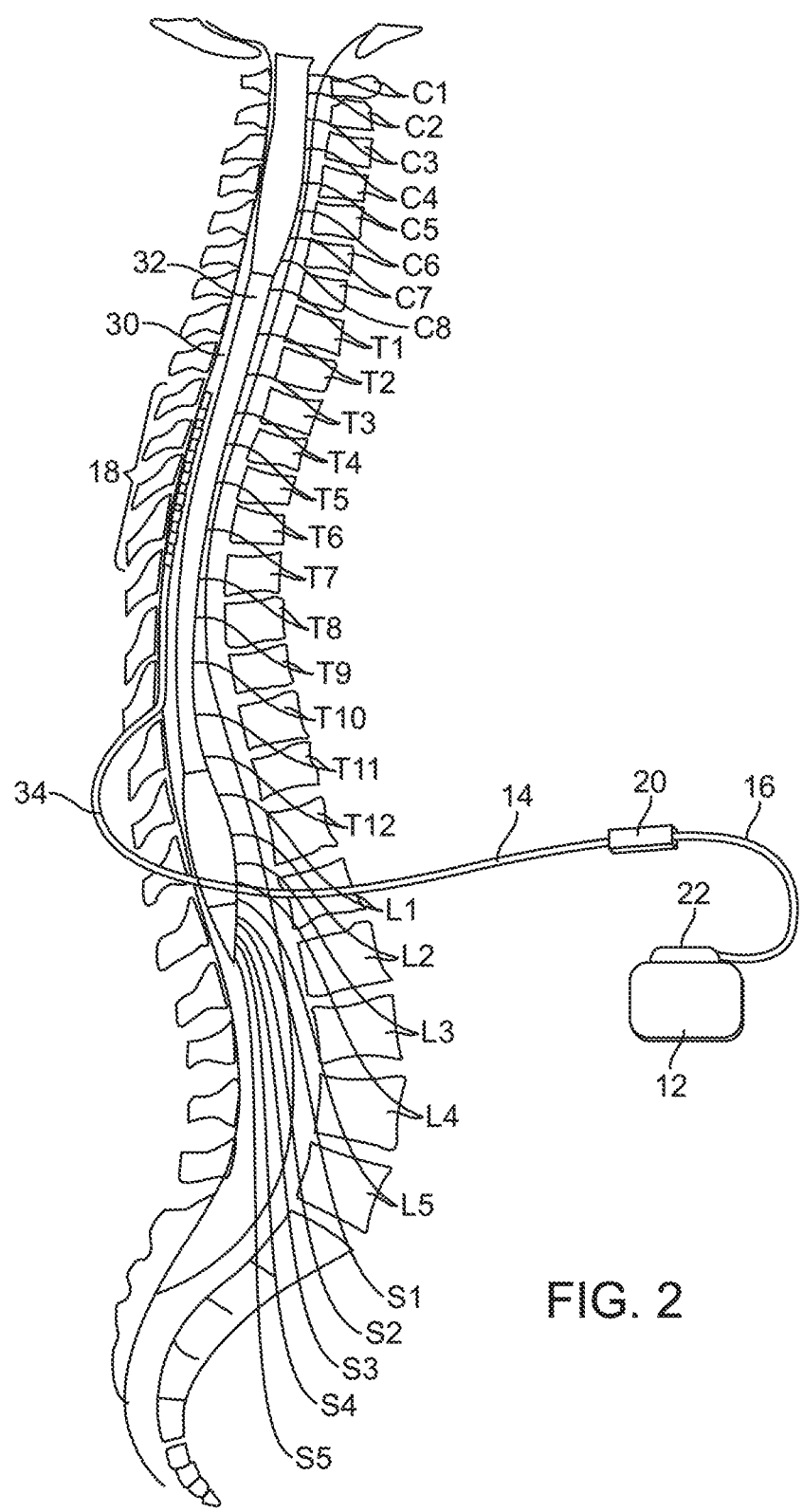
FIG. 2 is a plan view of the tissue stimulation system of FIG. 1 in use with a patient.

Referring first to FIGS. 1 and 2, a generalized tissue stimulation system 10 that may be used in spinal cord stimulation (SCS), as well as other stimulation applications, will be described. The stimulation system 10 generally comprises an implantable neurostimulator 12, an implantable stimulation lead 14, which carries an array of electrodes 18 (shown exaggerated for illustration purposes), and an implantable extension lead 16. These components can be provided in a kit that can then be assembled to create the stimulation system 10. Although only one stimulation lead 14 is shown, more than one stimulation lead, and typically two stimulation leads, can be used in the stimulation system 10. As there shown, the proximal end of the stimulation lead 14 is removably mated to the distal end of the extension lead 16 via a connector 20 associated with the extension lead 16, and the proximal end of the extension lead 16 is removably mated to the neurostimulator 12 via a connector 22 associated with the neurostimulator 12.

In the illustrated embodiment, the neurostimulator 12 takes the form of an implantable pulse generator (IPG) that comprises an electronic subassembly 24 (shown in phantom), which includes control and pulse generation circuitry (not shown) for delivering electrical stimulation energy to the electrodes (described below) of the stimulation lead 14 in a controlled manner, and a power supply, e.g., a battery 26 (shown in phantom), so that once programmed and turned on by an external programming device (not shown), the neurostimulator 12 can operate independently of external hardware.

Alternatively, the neurostimulator 12 can take the form of an implantable receiver-stimulator (not shown), in which case, the power source, e.g., a battery, for powering the implanted receiver, as well as control circuitry to command the receiver-stimulator, will be contained in an external controller inductively coupled to the receiver-stimulator via an electromagnetic link. Alternatively, the neurostimulator 12 can take the form of an external trial stimulator (ETS) (not shown), which has similar pulse generation circuitry as an IPG, but differs in that it is a non-implantable device that is used on a trial basis after the stimulation lead 14 has been implanted and prior to implantation of the IPG, to test the responsiveness of the stimulation that is to be provided.

The neurostimulator 12 comprises an outer housing 28 for housing the electronic and other components (described in further detail below), and the connector 22 to which the proximal end of the stimulation lead 14 (or optionally the proximal ends of the extension leads 16) mates in a manner that electrically couples the electrodes 18 to the pulse generation circuitry contained within the outer housing 28. The outer housing 28 is composed of an electrically conductive, biocompatible material, such as titanium, and forms a hermetically sealed compartment wherein the electronic subassembly 24 and battery 26 are protected from the body tissue and fluids. The connector 22 is disposed in a portion of the housing 28 that is, at least initially, not sealed.

The connector 22 carries a plurality of contacts (not shown) that come into electrical contact with the respective terminals (described in further detail below) of the stimulation lead 14 or extension lead 16 when the proximal end of the stimulation lead 14 or extension lead 16 is inserted into the connector 22. Electrical conductors (not shown), which extend from the connector 22 in electrical contact with the contacts, penetrate the housing 28 into the sealed chamber and connect to the electronic subassembly 24. Additional details discussing neurostimulators, including the outer housing 28 and connector 22, are disclosed in U.S. patent application Ser. No. 11/327,880, entitled "Connector and Methods of Fabrication," which is expressly incorporated herein by reference.

As shown in FIG. 2, the stimulation lead 14 is implanted in the epidural space 30 of a patient in close proximity to the spinal cord 32. Because of the lack of space near the lead exit point 34 where the stimulation lead 14 exits the spinal column, the neurostimulator 12 is generally implanted in a surgically-made pocket either in the abdomen or above the buttocks. The neurostimulator 12 may, of course, also be implanted in other locations of the patient's body. Use of the extension lead 16 facilitates locating the neurostimulator 12 away from the lead exit point 34. In addition, in some cases, the extension lead 16 may serve as a lead adapter if the proximal end of the stimulation lead 14 is not compatible with the connector of the neurostimulator 12 (e.g., different manufacturers use different connectors at the ends of their stimulation leads and are therefore not compatible with the connector heads of the neurostimulator of another manufacturer). The extension lead 16 may be made to adapt the stimulation lead 14 to connect the neurostimulator 12 to the stimulation lead 14, and hence, "adapt" the stimulation lead 14 to the neurostimulator 12. Thus, therapy can be conventionally provided to the patient by conveying electrical energy from the neurostimulator 12 to the electrodes 18, which electrical energy is then delivered to the spinal cord 32 adjacent the electrodes 18.

Figure 3:
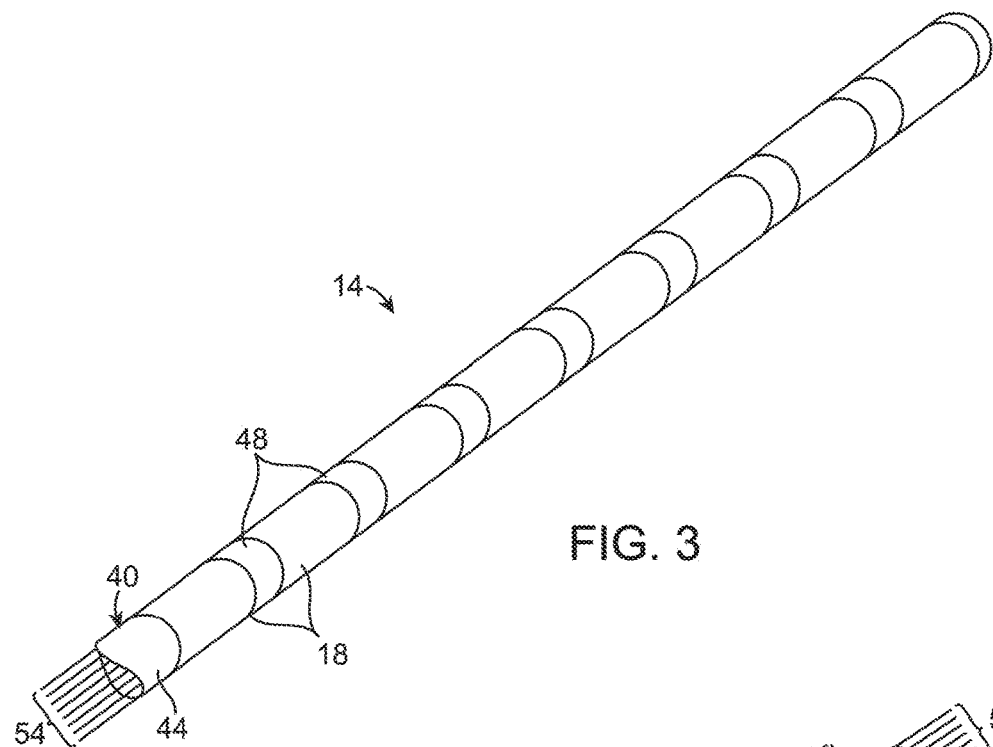
FIG. 3 is a perspective view of the distal end of a stimulation lead used in the tissue stimulation system of FIG. 1.
Figure 4:
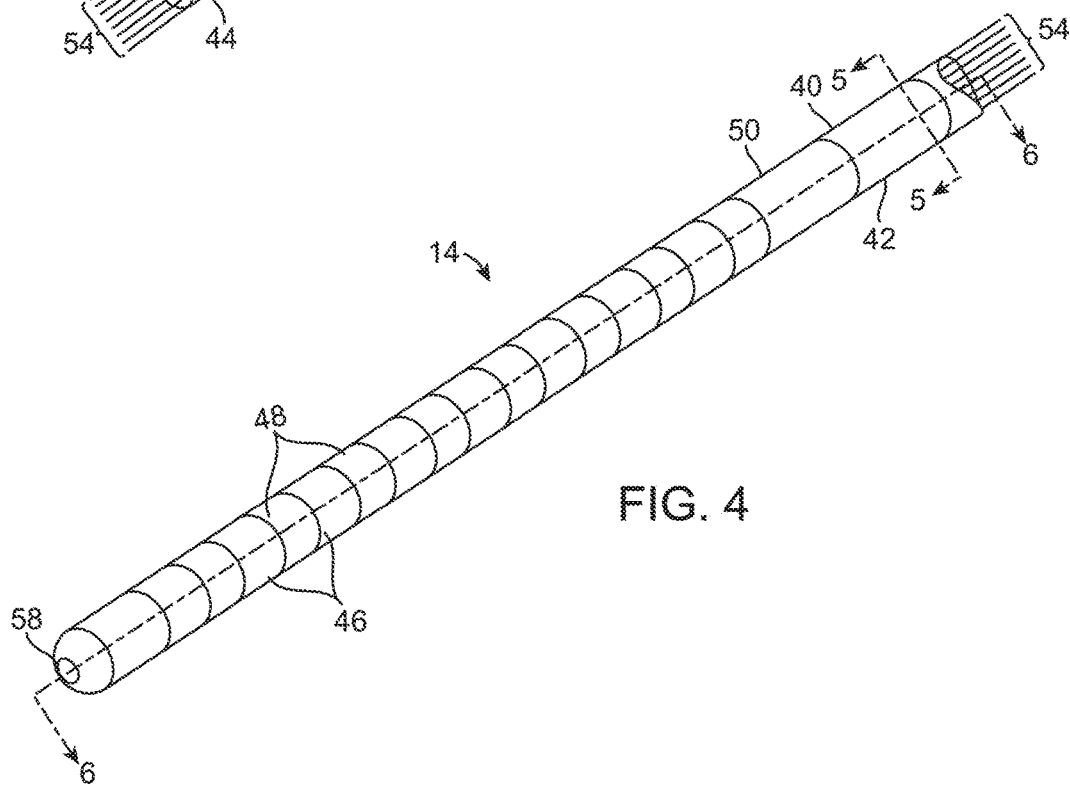
FIG. 4 is a perspective view of the proximal end of the stimulation lead used in the tissue stimulation system of FIG. 1.
Figure 5:
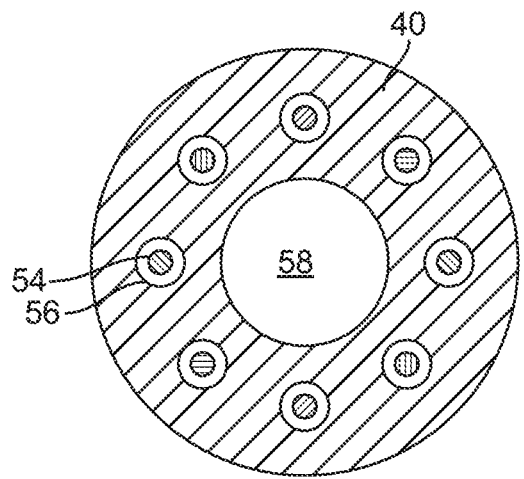
FIG. 5 is a cross-sectional view of the stimulation lead of FIG. 4, taken along the line 5-5.

Referring further to FIGS. 3-5, the stimulation lead 14 comprises an elongated tubular lead body 40 having a proximal end 42 and a distal end 44. The lead body 40 may, e.g., have a diameter of between about 0.03 inches to 0.07 inches and a length within the range of 30 cm to 90 cm for spinal cord stimulation applications. The lead body 40 may be composed of a suitable electrically insulative material, such as, a polymer (e.g., silicone, polyurethane, polytetrafluoroethylene (PTFE), or similar materials), and may be extruded from as a unibody construction.

The stimulation lead 14 further comprises a plurality of electrical contacts (in this case, the plurality of electrodes 18) mounted to the distal end 44 of the lead body 40 (FIG.

3), and a plurality of electrical terminals 46 mounted to the proximal end 42 of the lead body 40 (FIG. 4). In the illustrated embodiment, the stimulation lead 14 is a percutaneous lead, and to this end, the electrodes 18 are arranged in-line along the lead body 40. In an alternative embodiment, the stimulation lead may take the form of a single paddle lead (not shown), in which case the electrodes 18 may be arranged in a two-dimensional pattern on one side of a paddle.

Although the stimulation lead 14 is shown as having eight electrodes 18 (FIG. 3) and eight corresponding terminals 46 (FIG. 4), the number of electrodes and terminals may be any number suitable for the application in which the stimulation lead 14 is intended to be use (e.g., two, four, sixteen, etc.). In the illustrated embodiment, each of the electrodes 18 and terminals 46 takes the form of a cylindrical ring element composed of an electrically conductive, biocompatible, non-corrosive, material, such as, e.g., platinum, titanium, stainless steel, or alloys thereof.

The stimulation lead 14 further includes a plurality of electrically insulative spacers 48 located on the lead body 40 between the respective electrodes 18 and terminals 46. The spacers 48 may be composed of a suitable material, such as, a polymer (e.g., polyurethane or silicone). The stimulation lead 14 further includes a retention sleeve 50 located at the proximal end 42 of the lead body 40 just distal to the terminals 46. The retention sleeve 50 serves as a hard surface for a mechanical securing element, such as a set screw (not shown), used to secure the proximal end of the stimulation lead 14 within a connector (e.g., either carried by the extension lead or the neurostimulator). The stimulation lead 14 further comprises an optional radiopaque marker (not sown) located at the distal tip of the lead body 40.

The stimulation lead 14 also includes a plurality of electrical conductors 54 extending through individual lumens 56 within the lead body 40 and respectively connected between the electrodes 18 and terminals 46 using suitable means, such as welding, thereby electrically coupling the distally-located electrodes 18 to the proximally-located terminals 46. Each conductor 54 may be composed of a suitable electrically conductive material, such as platinum, titanium, stainless steel, or alloys thereof. In the illustrated embodiment, the conductor 54 is a multifilar cable (1×19 or 1×7) wire made from 28% inner core of pure silver with 78% outer cladding of MP35N stainless steel. The conductor 54 is then insulated with a thin outer jacket (0.001" thick) of Ethylene Tetrafluoroethylene (ETFE) fluoro-based polymer. In the illustrated embodiment, the conductors 54 can be pre-cut and two zones on the ETFE insulation pre-ablated where they are connected between the respective electrode 18 and terminal 46. The stimulation lead 14 further includes a central lumen 58 that may be used to accept an insertion stylet (not shown) to facilitate lead implantation.

Further details describing the construction of percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Further details regarding the construction of paddle leads are disclosed in U.S. patent application Ser. No. 11/319,291, entitled "Stimulator Leads and Methods for Lead Fabrication," the disclosure of which is expressly incorporated herein by reference.

Referring back to FIG. 1, the extension lead 16 is similar to the stimulation lead 14 in that it comprises an elongated lead body 60 having a proximal end 62 and a distal end 64, and a plurality of terminals (not shown) mounted to the proximal end 62 of the lead body 60. The lead body 60 of the extension lead 16 may be similarly dimensioned and constructed as the lead body 40 of the stimulation lead 14. The extension lead 16 may also include retention sleeve (not shown) much like the retention sleeve 50 of the stimulation lead 14.

The extension lead 16 differs from the stimulation lead 14 in that, instead of electrodes, it comprises the previously mentioned connector 20 mounted to the distal end 64 of the lead body 60. The connector 20 is configured to accept the proximal end 42 of the stimulation lead 14. As will be described in further detail below, the connector 20 carries a plurality of contacts that come into electrical contact with the respective terminals 46 of the stimulation lead 14 when the proximal end 42 of the stimulation lead 14 is inserted into the connector 20. In a similar manner as the stimulation lead 14 (shown in FIGS. 4 and 5), the extension lead 16 also includes a plurality of electrical conductors extending through individual lumens (both not shown) within the lead body 60 and connected between the respective terminals and contacts using suitable means, such as welding, thereby electrically coupling the proximally-located terminals with the distally-located contacts.

Referring now to FIGS. 6-16, specific details regarding the structure and method of manufacturing a stiffened proximal end of the stimulation lead 14 (or alternatively a stiffened proximal end of the extension lead 16) will now be described.

Figure 6:
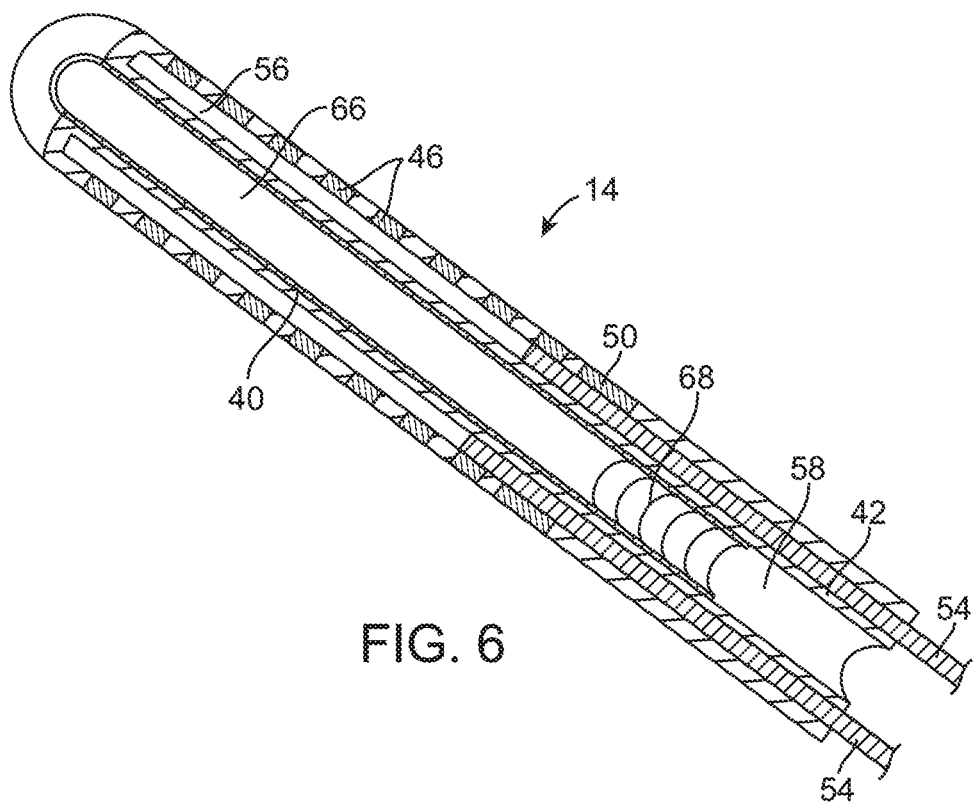
FIG. 6 is a cross-sectional view of the stimulation lead of FIG. 4, taken along the line 6-6.
Figure 7:
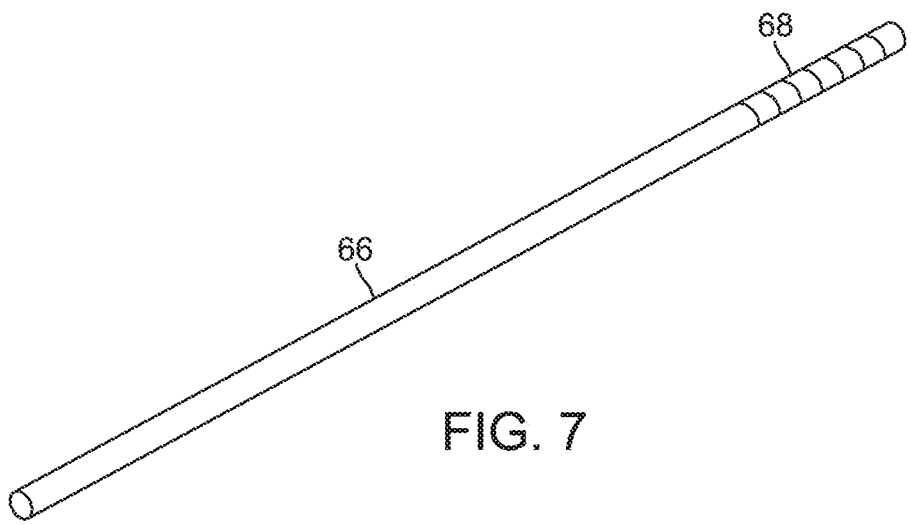
FIG. 7 is a perspective view of a stiffening tube used in the proximal end of the stimulation lead of FIG. 4.

Referring initially to FIGS. 6 and 7, the stimulation lead 14 further comprises an elongated stiffening tube 66 mounted within the proximal end 42 of the lead body 40. The stiffening tube 66 is composed of a material, such as, e.g., stainless steel, that has a higher stiffness than does the lead body 40. In the illustrated embodiment, the stiffening tube 66 is in a concentric relationship with the lead body 40 and surrounds the central lumen 58. To this end, the inner diameter of the stiffening tube 66 may be substantially the same as the diameter of the central lumen 58. Alternatively, the stiffening tube 66 may be disposed within the central lumen 58; that is, the outer diameter of the stiffening tube 66 may be substantially the same as the diameter of the central lumen 58. In either event, the stiffening tube 66 extends from a point that is proximal to the terminals 46 to a point that is just distal to the terminals 46, thereby stiffening the stimulation lead 14 along the terminals 46. The stiffening tube 66 may be retained within the lead body 40 using suitable means, such as an interference fit, adhesive bonding, or "re-flow" type forming to melt the lead body 40 around the stiffening tube 66, thereby locking it to the lead body 40.

As a result, the proximal end 42 of the lead body 40 may be easily inserted into a connector while minimizing the chance that the stimulation lead 14 will buckle in response to the frictional force applied to the lead body 40 by the connector. In the illustrated embodiment, the stiffening tube 66 extends to a point at the retention sleeve 50, which, as described above, will be frictionally engaged within the connector via a set screw. Thus, the stiffening tube 66 will be completely disposed within the connector when the proximal end 42 of the lead body 40 is fully received within the connector (i.e., the electrical contacts of the connector will have respectively engaged the electrical terminals 46 of the stimulation lead 14). As a result, maximum flexibility is provided to the stimulation lead 14 outside of the connector.

The stimulation lead 14 further comprises a coil 68 mounted within the proximal end 42 of the lead body 40 distal to the stiffening tube 66. In the illustrated embodiment, the coil 68 is affixed to stiffening tube 66. For example, the coil 68 can be welded to the stiffening tube 66 or may be machined or fabricated, such as via laser cutting, into the distal end of the stiffening tube 66. The stiffening tube 66 is formed from a helically shaped wire that may be composed of the same material as the stiffening tube 66. Due to the inherently structural nature of a coil, however, the coil 68 is more flexible than the stiffening tube 66. Like the stiffening tube 66, the coil 68 is in a concentric relationship with the lead body 40 and surrounds the central lumen 58. In the illustrated embodiment, the coil 68 has a length of between 0.25-1 inches, and thus, assuming that the stiffening tube 66 terminates at the retention sleeve 50, extends from the connector this distance when the proximal end 42 of the lead 14 is fully received within the connector.

Thus, the more flexible coil 68 provides a strain relief where the stiffening tube 66 terminates in the lead body 40. Furthermore, the flexible coil 68, in compression, adds strength to the lead body 40 just distal to the stiffening tube 66, which can be grasped by the physician when inserting the proximal end 42 of the lead body 40 into the connector.

Figure 8:
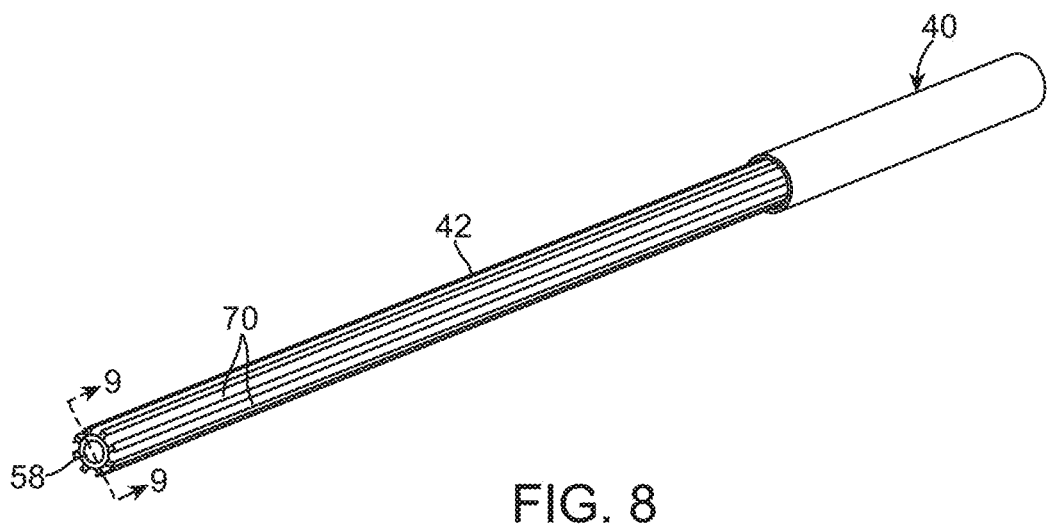
FIG. 8 is a perspective view of the proximal end of a lead body used in the proximal end of the stimulation of FIG. 4.
Figure 9:
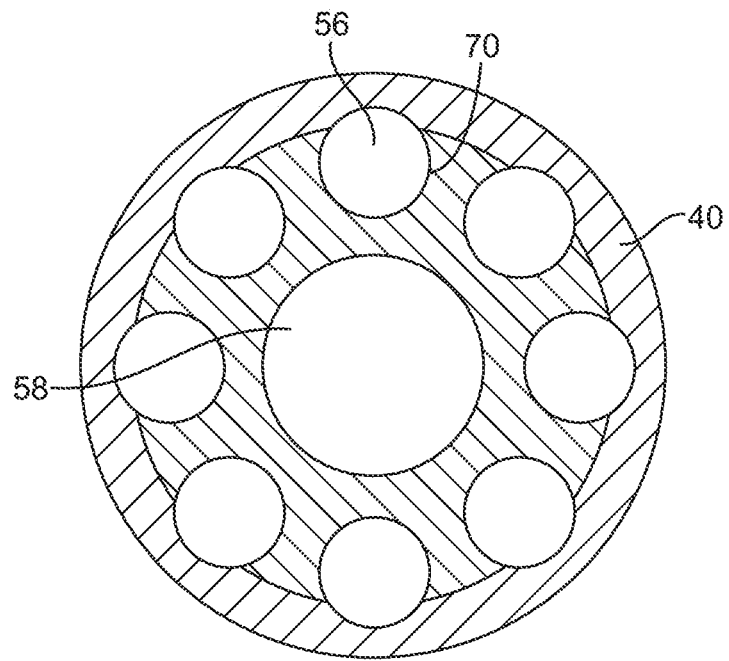
FIG. 9 is an axial view of the lead body of FIG. 4, taken along the line 9-9.
Figure 10:
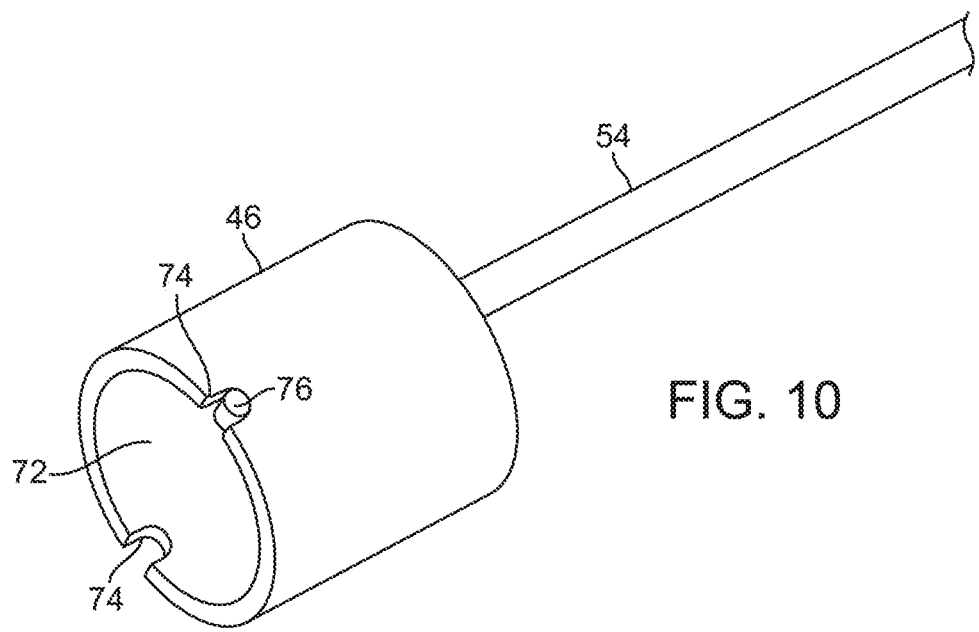
FIG. 10 is a perspective view of a terminal and associated electrical conductor used in the proximal end of the stimulation lead of FIG. 4.

Having described the structure of the proximal end of the stimulation lead 14, one method of its manufacture will now be described. Referring to FIGS. 8 and 9, axially disposed channels 70 are formed around the outer circumference of the proximal end 42 of the lead body 40. In the illustrated method, this can be accomplished by ablating the outer circumference of the lead body 40 until a portion of each of the lumens 56 is exposed to form the respective channels 70. Next, as illustrated in FIG. 10, each electrical conductor 54 is threaded through a lumen 72 of the ring-shaped terminal 46 and attached to the proximal end of the respective terminal 46 using suitable means, such as welding. In the illustrated embodiment, the proximal edge of each terminal 46 includes a notch 74 in which a curved portion 76 of the respective electrical conductor 54 is secured in order to strengthen the connection between the terminal 46 and conductor 54. Alternatively, the electrical conductor 54 may be "blind welded" o the lumen 72 of the respective of terminal 46.

Figure 11:
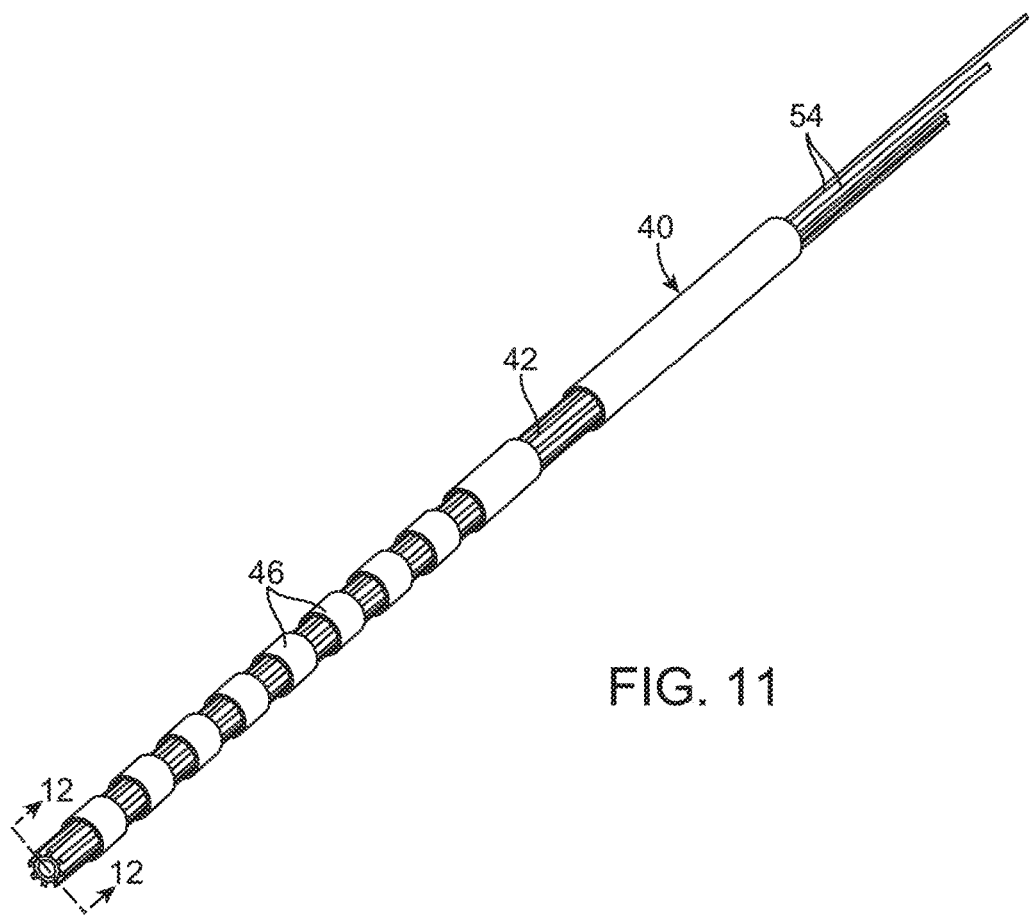
FIG. 11 is a perspective view of a subassembly of the lead body, electrical contacts, retention sleeve, and electrical conductors used in the proximal end of the stimulation lead of FIG. 4.
Figure 12:
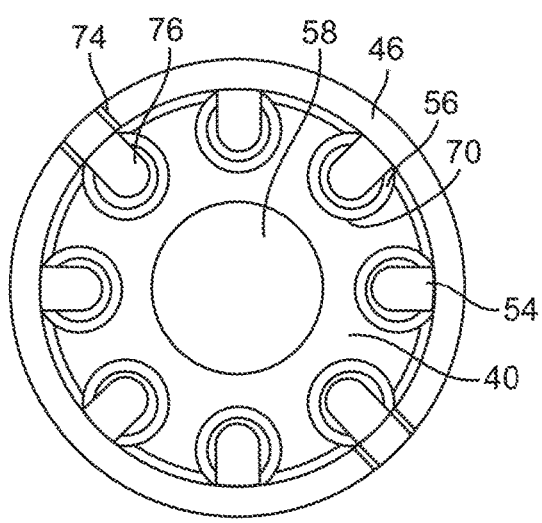
FIG. 12 is an axial view of the subassembly of FIG. 11, taken along the line 12-12.
Figure 13:
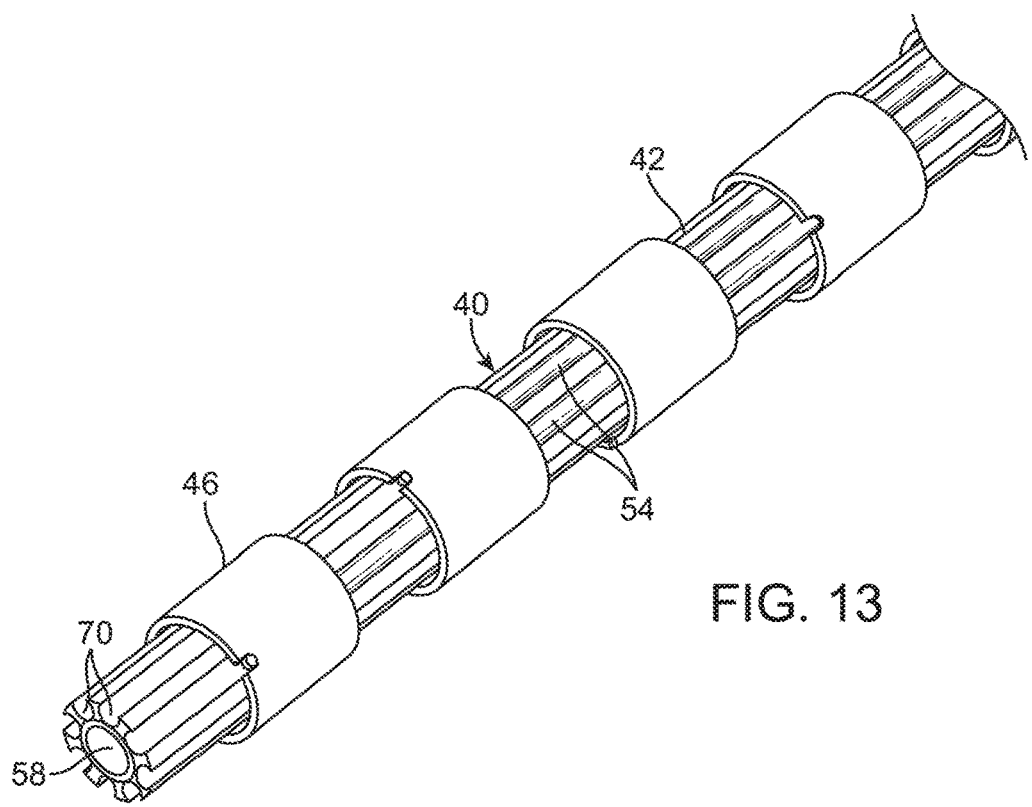
FIG. 13 is a close-up perspective view of the subassembly of FIG. 11.

Next, the retention sleeve 50, and then the terminals 46, along with the respectively attached electrical conductors 54, are threaded over the proximal end 42 of the lead body 40, as illustrated in FIGS. 11-13. While not shown, the spacers 48 (shown in FIG. 4) are also threaded over the proximal end 42 of the lead body 40 between the respective terminals 46. Each terminal 46 is rotationally oriented relative to the lead body 40 in a manner that places the respective attached electrical conductor 54 into a different channel 70. The electrical conductors 54 are also distally introduced from the channels 70 into the lumens 64 extending through the remainder of the lead body 40 and subsequently secured to the electrodes 18 (shown in FIG. 3) using a suitable means, such as welding. As best shown in FIG. 13, each channel 70 is deep enough, such that the electrical conductor 54 residing in the respective channel 70 does not come in contact with the terminals 46 disposed about the channels 70, but rather only comes into contact with the terminal 46 to which it is secured. Furthermore, the electrically insulative coating on the conductors 54 prevents short circuiting with adjacent terminals 46 if a conductor 54 happens to come in contact with the inner surface of the respective terminal 46.

Figure 14:
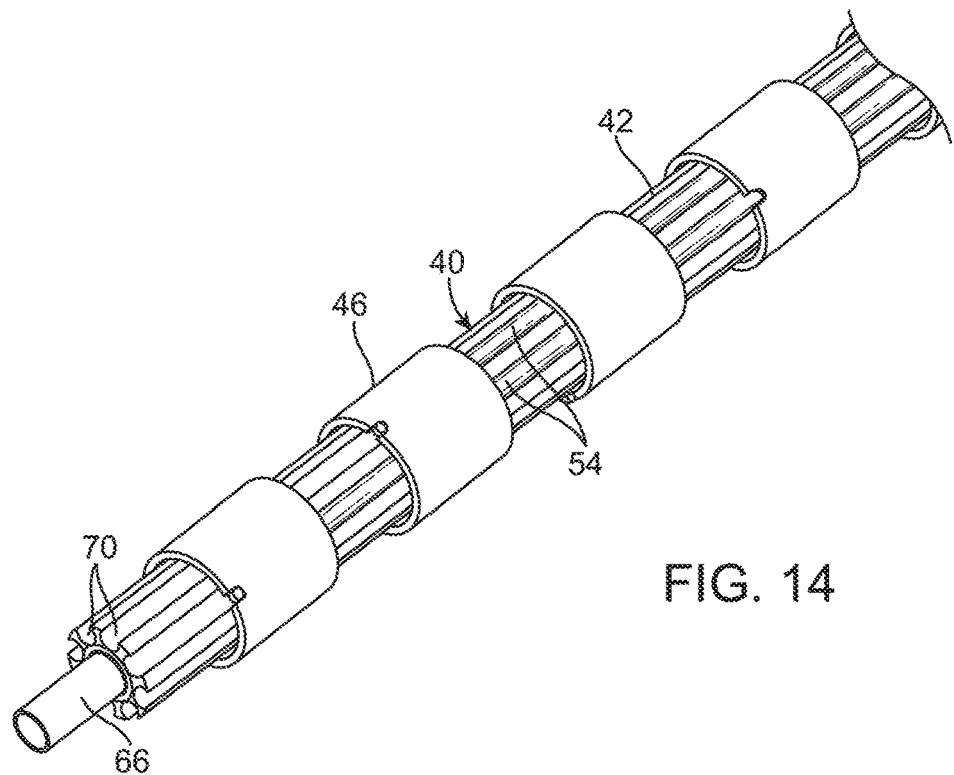
FIG. 14 is a close-up perspective view of the subassembly of FIG. 11, particularly showing the installation of a stiffening tube therein.

Next, as shown in FIG. 14, the stiffening tube 66 and associated coil 68 are introduced into the central lumen 58 until they are positioned relative to the terminals 46 and retention sleeve 50 in the manner described above. As there shown, a proximal portion of the stiffening tube 66 extends proximally from the lead body 40. Alternatively, the stiffening tube 66 can be completely inserted into the lumen 58. The spacers 48 (not shown in FIG. 14) are then reflowed (e.g., by exposing the assembly to a temperature between 140-250 degrees Celsius for a period of between 30-120 seconds). The proximal-most tip of the lead body 40 may be formed using an RF welder, or alternatively, can be formed during the reflow process. In addition, electrically insulative polyurethane monofilaments or other filler material, such as medical grade RTV silicone, can be introduced into the channels 70 and lumens 58 prior to reflow to better integrate the resulting assembly and ensure electrical isolation between the components. Significantly, the use of the stiffening tube 66 obviates the need to use rigid filler material, such as Hysol® epoxy, in order to stiffen the proximal end of the stimulation lead 14. Lastly, the terminals 46 and retention sleeve 50 are ground down or swaged to provide a uniform outer diameter, and thus, smoother outer surface, to the stimulation lead 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable electrical lead, comprising:
a lead body having a proximal end and a distal end;
a plurality of contacts disposed along the distal end of the lead body;
a plurality of terminals disposed along the proximal end of the lead body;
a plurality of conductors axially extending within the lead body and coupling the contacts to the terminals; and
a stiffening tube disposed within the proximal end of the lead body and beneath at least one of the terminals, wherein the stiffening tube defines a lumen extending through the stiffening tube and the stiffening tube terminates proximal to all of the contacts.

2. The implantable electrical lead of claim 1, wherein the lead body defines a central lumen extending from a proximal end of the lead body.

3. The implantable electrical lead of claim 2, wherein the stiffening tube has an inner diameter equal to a diameter of the central lumen.

4. The implantable electrical lead of claim 2, wherein the stiffening tube is disposed within the central lumen.

5. The implantable electrical lead of claim 4, wherein the stiffening tube has an outer diameter equal to a diameter of the central lumen.

6. A neurostimulation system, comprising:
the implantable electrical lead of claim 1; and
a connector configured for receiving the proximal end of the lead body, such that the connector is electrically coupled to the terminals of the implantable electrical lead.

7. The neurostimulation system of claim 6, wherein the stiffening tube is configured for being completely disposed within the connector when the proximal end of the lead body is fully received within the connector.

8. The neurostimulation system of claim 6, further comprising a neurostimulator, wherein the connector is part of the neurostimulator.

9. The neurostimulation system of claim 6, further comprising an extension lead that carries the connector, wherein the implantable electrical lead is a stimulation lead.

10. The implantable electrical lead of claim 1, wherein a portion of the stiffening tube forms a coil.

11. The implantable electrical lead of claim 10, wherein the coil is a distal portion of the stiffening tube.

12. The implantable electrical lead of claim 10, wherein the portion of the stiffening tube is laser cut into the coil.

13. The implantable electrical lead of claim 1, wherein the stiffening tube is disposed beneath all of the terminals.

14. The implantable electrical lead of claim 1, wherein the stiffening tube is composed of a metallic material.

15. The implantable electrical lead of claim 1, further comprising a coil affixed to the stiffening tube.

16. The implantable electrical lead of claim 1, further comprising a retention sleeve mounted to the proximal end of the lead body distal to the terminals, wherein the stiffening tube terminates in the lead body at or distal to the retention sleeve.

17. The implantable electrical lead of claim 1, wherein the stiffening tube extends from a point proximal to the terminals to a point just distal to the terminals.

18. The implantable electrical lead of claim 1, wherein the stiffening tube is made of a material having a higher stiffness than the lead body.

19. The implantable electrical lead of claim 1, wherein the contacts are electrodes and the implantable electrical lead is a stimulation lead.

20. The implantable electrical lead of claim 1, further comprising a connector disposed along the distal end of the lead body, wherein the implantable electrical lead is an extension lead.

* * * * *